United States Patent [19]

Lang et al.

[11] Patent Number: 5,372,606
[45] Date of Patent: Dec. 13, 1994

[54] METHOD AND APPARATUS FOR GENERATING ADAPTIVE N-PHASIC DEFIBRILLATION WAVEFORMS

[75] Inventors: Douglas J. Lang, Arden Hills, Minn.; David K. Swanson, Mountain View, Calif.

[73] Assignee: Cardiac Pacemakers, Inc., St. Paul, Minn.

[21] Appl. No.: 132,947

[22] Filed: Oct. 7, 1993

[51] Int. Cl.$^5$ .............................................. A61N 1/36
[52] U.S. Cl. ............................................ 607/6; 607/8
[58] Field of Search .............................. 607/5, 6, 7, 8

[56] References Cited

U.S. PATENT DOCUMENTS

| | | |
|---|---|---|
| 4,800,883 | 1/1989 | Winstrom . |
| 4,821,723 | 4/1989 | Baker, Jr. et al. . |
| 4,850,357 | 7/1989 | Bach, Jr. . |
| 5,083,562 | 1/1992 | de Coriolis et al. . |

Primary Examiner—William E. Kamm
Assistant Examiner—Scott M. Getzow
Attorney, Agent, or Firm—Keck, Mahin & Cate

[57] ABSTRACT

A method and apparatus for delivering an adaptive n-phasic waveform to the heart in either a fixed-tilt delivery mode or a fixed-duration delivery mode. A first phase of a first polarity is delivered to the heart. The first phase is set to terminate upon decaying to a preset level. If the first phase does not decay to the preset level within a predetermined maximum period of time, the first phase is terminated and the subsequent phases are delivered in a fixed-duration delivery mode. Because the first phase did not decay fast enough, it is determined that the patient has a relatively high system impedance. Therefore, subsequent phases will be delivered to the patient in a fixed-duration mode to insure the defibrillation is reversed. Otherwise, if the first phase decays to the preset level in less than the maximum predetermined period of time, it is determined that the patient has a relatively low system impedance and subsequent phases should be delivered in a fixed-tilt mode.

15 Claims, 3 Drawing Sheets

METHOD AND APPARATUS FOR GENERATING ADAPTIVE N-PHASIC DEFIBRILLATION WAVEFORMS

BACKGROUND OF THE INVENTION

The present invention relates to an adaptive method and apparatus for n-phasic truncated-exponential defibrillation that optimizes the shock delivery technique based on a patient's system impedance.

In conventional defibrillators, defibrillation waveforms are delivered in one of a fixed-tilt or fixed-duration format. As is well known in the art, an n-phasic waveform comprises consecutive pulses of opposite polarity. Characteristics of an n-phasic defibrillation waveform include the rate or angle of decay of an individual pulse (often referred to as the "tilt," where tilt=$((V_i - V_f)(V_i) \times 100\%)$ and the duration of each individual pulse. In devices using the fixed-duration format, the duration of each pulse is fixed but the tilt of each pulse varies with patient system impedance. See, for example, U.S. Pat. Nos. 4,800,883 to Winstrom and 4,821,723 to Baker, Jr. et al. Studies have shown that the defibrillation energy increases as the trailing edge voltage becomes lower, like that associated with low patient system impedances. A drawback of the fixed duration technique is that for patients with low impedances, shock durations must be manually programmed to shorter values to prevent the tilts from becoming too large, creating low trailing voltages.

In devices which use the fixed-tilt format, the individual pulses of the n-phasic waveform have durations that vary with patient system impedance. See, for example, U.S. Pat. No. 4,998,531, granted Mar. 12, 1991, to Bocchi et al. This type of device avoids low trailing edge voltage by automatically varying the duration. However, it is sometimes unnecessary to continue capacitor discharge beyond the 15-20 msec duration. While the longer durations for fixed-tilt waveforms at high impedances are not detrimental, they do have the disadvantage of delivering unneeded extra energy to the patient.

While some defibrillation systems utilize fixed-tilt or fixed-duration shock delivery techniques, there is no system heretofore known which combines the principles of both of these techniques. Fixed-duration devices require manual programming to assure correct waveforms at low impedances. Fixed-tilt devices do not incorporate a time limit for switching to an alternative shock delivery method. Combining the best features of both techniques into a device with adaptive n-phasic waveforms yields a therapy option that is automatically optimized for each patient.

SUMMARY OF THE INVENTION

It is a primary feature of the present invention to provide a method and apparatus for n-phasic defibrillation capable of automatically selecting the particular defibrillation duration and tilt parameters to minimize the defibrillation energy requirements.

It is an additional feature of the present invention to provide a method and apparatus for generating n-phasic truncated defibrillation waveforms which adjust to the magnitude of the patient's system impedance to minimize the level of the defibrillation energy delivered to the patient.

It is a further feature of the present invention to provide a method for defibrillating the heart by combining the advantages of a fixed-tilt defibrillation mode and a fixed-duration defibrillation mode into a single adaptive n-phasic device to provide a therapy option that is automatically optimized for each patient.

The n-phasic defibrillation system and method of the present invention is adaptable to shock a patient with low impedances in a fixed-tilt mode with variable duration and to shock a patient with higher impedances in a fixed-duration mode with variable waveform tilt. The shape of the waveform is programmable by specifying the percentage duration of a particular phase relative to the overall duration or by specifying the percentage voltage tilt at the termination of a particular phase relative to the initial capacitor voltage. In addition, a maximum time switch duration is programmable corresponding to the maximum amount of time the system stays in the fixed-tilt mode before switching to the fixed-duration mode. Thus, by setting a maximum limit on the duration of the shock, the adaptive method of the present invention optimizes energy delivered to the patient. Furthermore, by switching to a fixed-duration mode at higher impedances, waveforms, e.g., that are more rectangular (having higher trailing edge voltages), may be produced.

Once an arrhythmia is initially detected, a n-phasic shock is delivered to the patient initially in the fixed-tilt mode. If the particular patient has a low patient system impedance or capacitance, the voltage will decrease below the preset tilt level before the maximum time duration allowed for that particular phase. Thus, the waveform will reverse polarity and enter the next phase within the maximum time duration. However, if the patient has a relatively high system impedance or capacitance, the voltage will take longer to decrease below the preset tilt level and the phase will likely exceed the preset maximum time switch duration. In this case, the system is designed to switch to a fixed-duration mode to terminate that phase and switch polarity to a new phase. This both avoids delivering more energy to the patient than is necessary (as would occur in a fixed-tilt waveform), and minimizes risks from long duration trailing edges and low cardiac current densities reinitiating fibrillation. Thus, patients with higher system impedances or capacitances will appropriately receive the waveform in a fixed-duration mode.

The above and other objects and advantages of the present invention will become more readily apparent when reference is made to the following description taken in conjunction with the accompanying drawings.

DETAILED DESCRIPTION OF THE DRAWINGS

Figure 1:
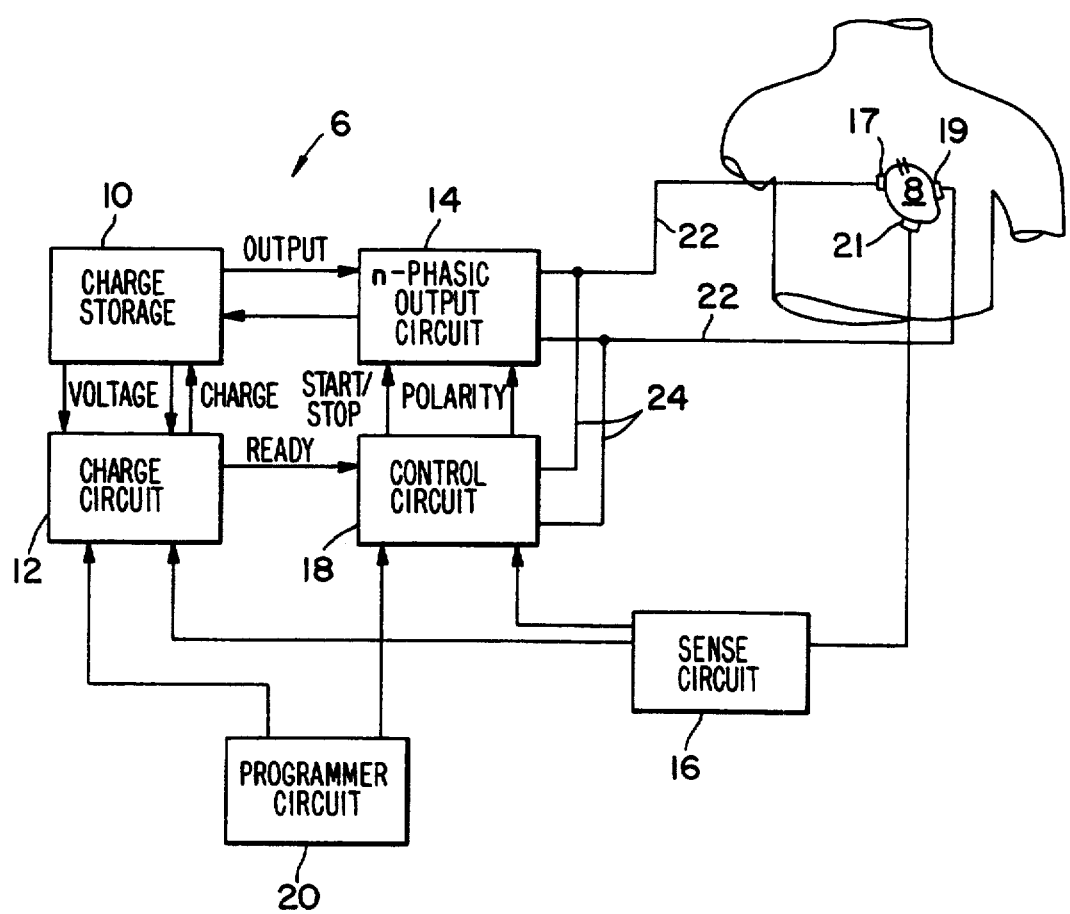
FIG. 1 is schematic block diagram of the adaptive n-phasic defibrillation system according to the present invention.

The adaptive n-phasic defibrillation system according to the present invention is illustrated in FIG. 1 and is generally shown at 6. The system 6 includes a capacitor or other charge storage device 10, a charge circuit 12 for charging the capacitor 10 to a predetermined voltage, an n-phasic output circuit 14 which delivers the charge on the capacitor 10 to the discharge electrodes 17 and 19 via leads 22 with pulses of either polarity, and a sense circuit 16 which monitors the electrical activity of the heart and is responsive to an arrhythmia in the heart 8. A sensing electrode 21 is provided to sense the electrical activity of the heart and convey this information to the sense circuit 16. A control circuit 18 is provided which determines when and with which polarity a pulse is to be delivered, based on input from the sensing circuit 16 and the instantaneous measurement of shock voltage and duration. The control circuit 18 includes a counter (not shown) which counts the number of phases delivered. Lines 24 connect the control circuit to the electrode lead lines 22 for obtaining the instantaneous values of shock voltage and elapsed time.

A programmer circuit 20 is provided which is connected to the charge circuit 12 and the control circuit 18 to program the values of certain parameters governing the function of the system. Specifically, the initial voltage of the capacitor ($V_o$) and the number of phases in the waveform (n). In addition, certain parameters describing the waveshape are also programmed. The waveshape may be described by the tilt of a particular phase or the relative duration of a particular phase. The minimum voltage of a particular phase, $V_{k,min}$, is specified by a ratio between the voltage level at the end of that phase and the voltage level to which the capacitor is initially charged. Similarly, the duration of a particular phase can be specified as a ratio of the duration of the first phase relative to the duration of the first phase $t_{k(k=1,n)}$. Alternatively, the duration of a particular phase is specified as a percentage of the total duration of the pulsing sequence.

The shape of a particular phase may be described by the voltage tilt or relative phase duration. The phase duration can be computed from the voltage tilt, and the voltage tilt can be computed from the phase duration. Therefore, to describe the shape of an n-phasic pulse sequence, only n+2 parameters are required (the initial voltage $V_o$ and the minimum final voltage of the first phase, the maximum duration of the first phase $t_{1,max}$ and the relative duration of each of the remaining n−1 phases). One need not specify both sets of parameters to program the device. A microprocessor or other similar device may be used from the programmer circuit 20. These devices would compute the necessary $t_k$ and $V_{k,min}$ values based on the above programmed data, and determine the absolute time durations for each pulse ($t_{kmax}$).

In addition, the programming circuit 20 is used to program the initial voltage of the first phase $V_o$ and the maximum allowed duration before switching from a fixed-tilt mode to a fixed-time mode. This parameter is given in terms of the maximum absolute duration of the first phase $t_{1,max}$ before switching from fixed tilt delivery to fixed-time delivery. (This facilitates a shorter first phase.) Thus, n+2 parameters are needed to describe an adaptive n-phasic waveform according to the present invention.

Figure 2:
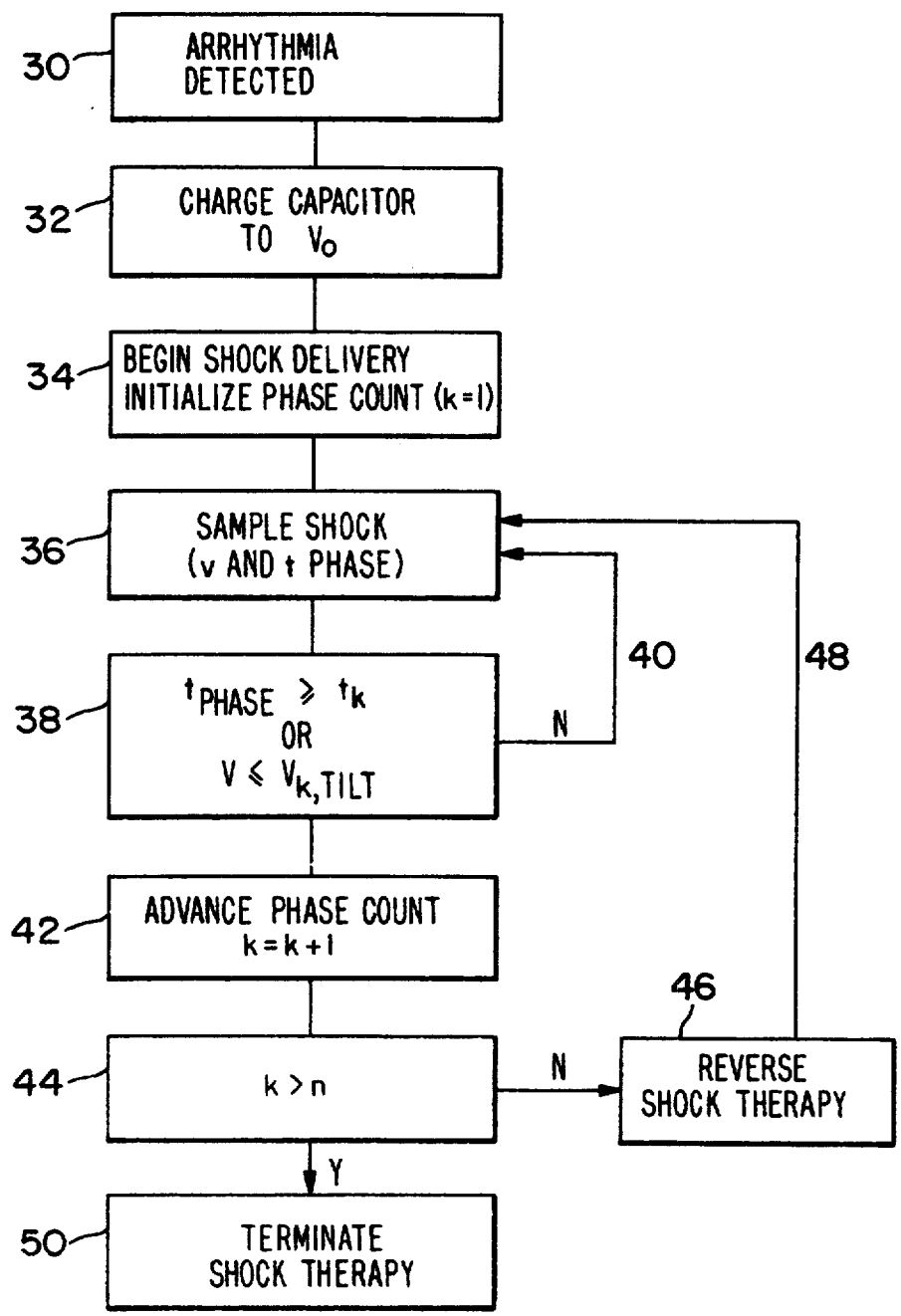
FIG. 2 is a flow diagram illustrating the adaptive n-phasic defibrillation method according to the present invention.

Referring to FIG. 2, the adaptive n-phasic shock delivery method according to the present invention will now be described. When an arrhythmia condition exists in the heart 8, the sensing circuit 16 signals the charge circuit 12 and control circuit 18 for declaring the occurrence of an arrhythmic condition in step 30. The capacitor 10 is then charged to a predetermined voltage $V_o$ by the charge circuit 12 in step 32. Once the capacitor 10 is charged to the predetermined voltage, the charge circuit 12 signals the control circuit 18 to initiate shock delivery in an initial predetermined polarity through the n-phasic output circuit 14 and initializes the phase count k (k=1) in step 34. The control circuit 18 monitors the voltage and elapsed time (duration) of the waveform in step 36. Each time the waveform is sampled, two tests are made by the control circuit 18 in step 38: (1) Is the cumulative time duration in the current phase ($t_k$) greater than the maximum absolute duration set for that particular phase($t_{k,max}$) before polarity reversal; and (2) is (the magnitude of) the relative shock voltage V less than or equal to the predetermined minimum voltage ($V_{k,tilt}$) selected for polarity reversal for that particular phase.

Fixed-tilt Delivery Mode

The delivery mode is determined by the rate at which the waveform voltage decays. Patients with faster decay rates (those with smaller system capacitances or impedances) will use the fixed-tilt delivery mode since the pulses in these systems will satisfy the tilt criterion before the time criterion, making the pulses shorter than or equal to the programmed maximum phase durations. With this mode of delivery, the waveforms will be determined by the voltage comparisons $V < V_{k,min}$ in step 38.

The system is designed so that the fixed-tilt delivery mode is assumed to be the first operation mode. In this regard, the first phase is used as a test phase for determining the system impedance of the patient. By starting in a fixed-tilt mode, if the decreasing shock voltage has not reached the predetermined maximum voltage selected for polarity reversal for that particular phase, capacitor discharge continues without a change in polarity in step 40. However, when the voltage V becomes less than or equal to $V_{k,min}$, the phase count k is incremented in step 42 and the count is compared to the predetermined number of phases n in step 44. If k≤n, the control circuit 18 signals the n-phasic output circuit 14 to reverse shock polarity in step 46, and capacitor discharge is continued by communication link 48 with continued voltage and duration monitoring in step 36. If, on the other hand, k>n, then the control circuit 18 signals the output circuit 14 to truncate the waveform and stop shock delivery in step 50.

Fixed-duration Delivery Mode

Systems with slower decay rates (those with higher capacitances or impedances) will use the fixed-duration delivery mode since the phase durations will reach the maximum programmed duration limits, $t_{k,max}$, before the pulse voltages can reach the tilt voltage limits, $V_{k,min}$. Similarly, it is possible to adjust the programming features so the system will initially assume the fixed duration delivery mode and switch to the fixed-tilt mode upon a predetermined decrease in shock voltage. With this mode of delivery, the waveforms will be determined by the time duration comparisons. In step 38, if the phase duration is greater than its maximum value, $t_{k,max}$, the current phase is terminated in step 42. The control circuit 18 increments the phase count k and compares it to the number of predetermined phases, k>n in step 44. If the preset number of phases has been delivered, the shock is terminated in step 50. If more phases are to be included, the shock polarity is reversed in step 46, after which capacitor discharge is continued in step 48 with time and voltage monitoring in step 36.

When the decay rate of the shock voltage is slow, each phase will be delivered until its duration equals the maximum set duration $t_{k,max}$. In this case the voltage criterion will never be satisfied, since $V > V_{k,min}$ for all phases due to the slow voltage decay of the system.

Figure 3:
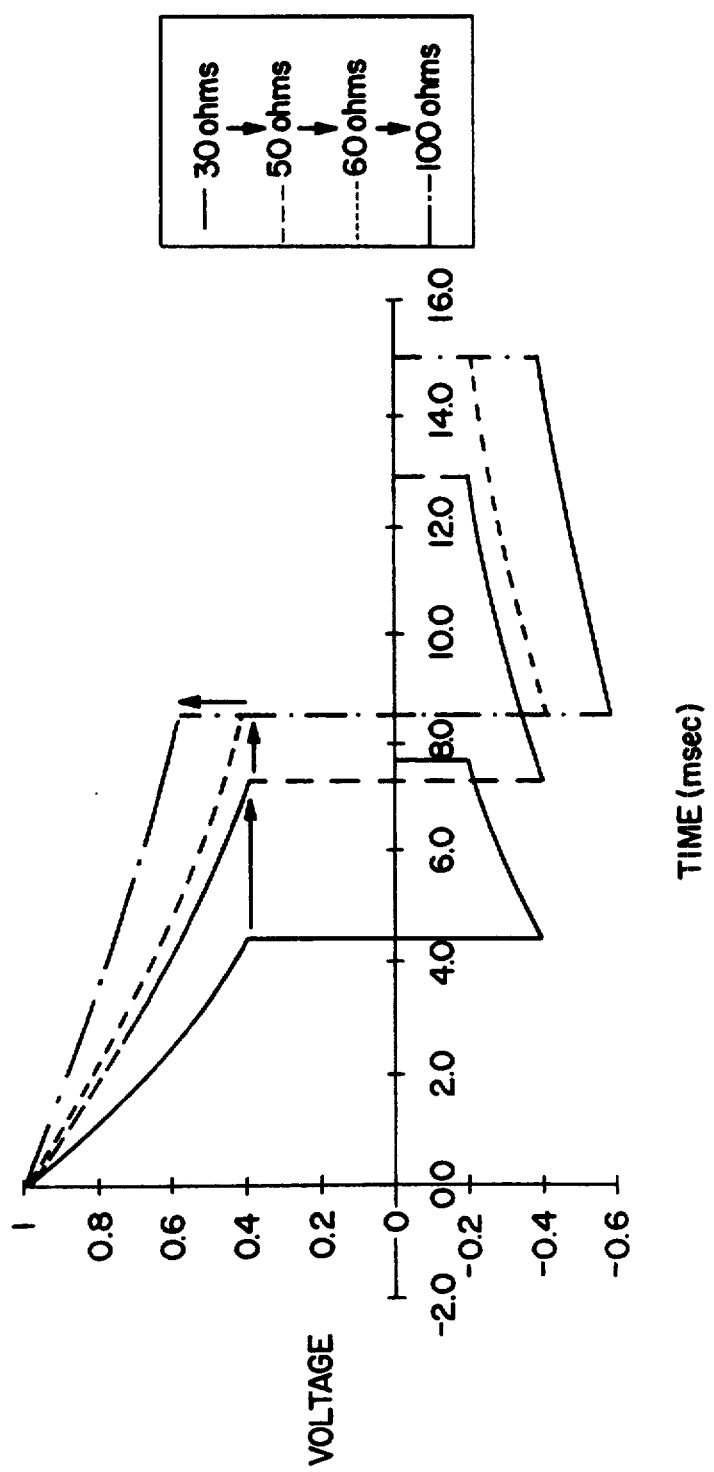
FIG. 3 is a graph illustrating a biphasic defibrillation waveform generated by the n-phasic defibrillation system and method according to the present invention.

An adaptive n-phasic waveform produced by the system and method according to the present invention is illustrated in FIG. 3. In this figure, the initial programmed parameters are:

initial capacitor charge voltage $V_o = 1.0$;
number of phases $n = 2$;
percentage change in voltage at the end of each phase: $V_{1,min} = 40\%$, $V_{2,min} = 20\%$.

By specifying the relative voltages, it is possible to automatically determine the relative pulse widths of the various phases. The duration of the first and second phases ($t_1$ and $t_2$) of a fixed-tilt waveform are related to the voltage tilts by the expressions:

$$t_{1,max} = -\tau ln(V_{1,min});$$

$$t_{2,max} = -\tau ln(V_{2,min}/V_{1,min});$$

where ln is the natural logarithm and $\tau$ is the patient system time constant which is equal to the product of the system capacitance and the patient system impedance. It is not necessary to determine the value of the patient system time constant $\tau$ to program the system parameters. This constant is described above only as a means for illustrating the relationship with the data specifying the tilt voltages.

In FIG. 3, the tilt voltages given above result in a second phase duration to be 75.6% of the duration of the first phase ($t_2 = (t_{2,max}/t_{1,max})*t_1$). Similar ratios for $t_k$ can be calculated between each phase duration, $t_k = \tau ln(V_{k,min}/V_{k-1,min})$, and the maximum duration of the first phase, $t_{1,max}$ as follows: $t_k = (t_{k,max}/t_{1,max})*t_1$. The duration of each phase, $t_k$, may be less than or equal to the maximum duration programmed for that particular phase $t_{k,max}$, depending on the time constant of the system.

In the present invention, the phase duration ratios specified by the programmed data are used for both the fixed-tilt and fixed-duration shock delivery methods. For fixed-tilt delivery where $t_k \leq t_{k,max}$, the relative phase durations are always maintained, since the voltage comparisons automatically produce the relative phase relationships. For the fixed-duration delivery mode, the duration of the first phase equals $t_{1,max}$. The durations of all subsequent phases, $t_{k,max}$, are calculated by the control circuit 18 using the phase duration ratios $t_k$ defined above for fixed-tilt waveforms by the expression $t_{k,max} = (t_k/t_1)t_{1,max}$.

For the waveforms shown in FIG. 3, the maximum duration of the first phase is set at 8.6 msec. So long as the system impedance is between 30 to 60 ohms, the mode of delivery is fixed-tilt (variable duration), since the duration of the first phase never exceeds $t_{k,max} = 8.6$ msec. However, for impedances greater than 60 ohms, the first phase duration for a fixed-tilt delivery method is greater than 8.6 msec, so that the delivery mode switches from the fixed-tilt mode to the fixed-duration shock mode with the second phase duration timed so that $t_{2,max} = 0.756*t_{1,max}$. As impedance rises from 60 to 100 ohms, the trailing edge voltages rise from 0.4 to 0.59 and 0.2 to 0.39 for phases 1 and 2, respectively. Pulse width ratios are similar for both delivery methods.

This adaptive method for delivering n-phasic defibrillation waveforms has several advantages over the standard fixed-tilt or fixed-duration methods. For low impedances, the method and system according to the present invention automatically adjusts shock duration according to the patient system impedance, avoiding low trailing edge voltages that may refibrillate the patient's heart. The fixed-tilt shock mode delivers a constant energy shock to the patient, independent of impedance. Defibrillation energy requirements may remain essentially constant for bi-phasic fixed-tilt shock durations between 5 and 15 msec. Thus, the present invention shares the advantage of other fixed-tilt methods for moderate to low system impedances in that it automatically delivers the correct amount of energy for defibrillation, independent of impedance. By avoiding additional programming of phase durations and amplitudes, this adaptive method becomes more "user friendly" for managing arrhythmia patients with low impedances or impedances that change with implant duration.

For high impedances, the present adaptive method shares the advantages of fixed duration delivery. Defibrillation with fixed-tilt waveforms may require a constant voltage for shock durations greater than 15–20 msec. In such cases, the longer durations of a fixed-tilt waveforms at higher impedances ($>20$ msec) are not necessary for defibrillation success, and often result in delivering more energy to the patient than is needed. The adaptive method according to the present invention may minimize the energy delivered to the patient by setting a maximum limit on the duration of the shock. If the first phase of the waveform reaches this maximum duration, shock delivery switches to a fixed-duration mode to minimize energy transfer.

Defibrillation energies may also increase with long duration fixed-tilt shocks ($t > 20$ msec) which occur at high impedances. This may be due to the low current densities in the heart during the trailing edges of the waveform. These low currents may reinitiate fibrillation, reducing the effectiveness of long fixed-tilt defibrillation waveforms. The adaptive n-phasic delivery method of the present invention has the advantage of cutting off the pulse earlier with higher trailing edge currents, reducing the chance of low current density in the heart that may reinitiate fibrillation.

An additional benefit of the adaptive delivery method according to the present invention is that switching to a fixed-duration mode at higher impedances produces waveforms that are more rectangular (trailing edge voltages are higher). Defibrillation thresholds may decrease or remain unchanged as these trailing edge voltages are elevated. In such cases, adaptive n-phasic waveforms not only minimize energy delivered, but may also lower defibrillation thresholds at higher impedances.

The foregoing description is intended by way of example only and is not intended to limit the present invention in any way except as set forth in the following claims.

We claim:

1. A method for delivering an adaptive n-phasic defibrillation waveform to the heart comprising the steps of:

monitoring the electrical activity of the heart;
setting a predetermined maximum amount of time for which a first phase of said n-phasic defibrillation waveform may last;
delivering said first phase of said n-phasic defibrillation waveform to the heart upon detecting an arrhythmia of the heart in a fixed-tilt delivery mode so that said first phase terminates upon the level of said first phase decreasing to a preset level;

monitoring the time duration of said first phase;

terminating said first phase and switching to a fixed-duration delivery mode if the time duration of said first phase is greater than or equal to said predetermined maximum amount of time;

delivering phases of said n-phasic defibrillation waveform, subsequent said first phase, in alternating polarities to the heart in a fixed-duration delivery mode if the time duration of said first phase is greater than or equal to said predetermined maximum amount of time whereby each of said subsequent phases terminates upon the duration of the phase meeting a preset value; and delivering phases of said n-phasic defibrillation waveform, subsequent said first phase, and in alternating polarities to the heart in a fixed-tilt mode if the time duration of said first phase is not greater than or equal to said predetermined maximum amount of time whereby each of said subsequent phases terminates upon the level of the phase decreasing to a preset value.

2. The method of claim 1, and further comprising the steps of:

presetting the total duration of said n-phasic defibrillation waveform; and presetting the waveshape of each of said phases of said n-phasic defibrillation waveform by setting the duration of each of said phases as a percentage of the total duration of said n-phasic defibrillation waveform.

3. The method of claim 1, further comprising the step of:

presetting the waveshape of each phase subsequent said first phase by setting the duration of said each phase as a percentage of the duration of the first phase.

4. The method of claim 3, wherein said percentage is determined by the preset value for said each phase divided by the predetermined maximum amount of time of the first phase.

5. The method of claim 1, and further comprising the steps of:

providing a defibrillation capacitor;

presetting the initial voltage level of said defibrillation capacitor, said initial voltage level being an initial voltage level of said first phase of said n-phasic defibrillation waveform; and presetting the waveshape of each of said phases of said n-phasic defibrillation waveform by setting the voltage tilt of each of said phases as a percentage of the initial voltage level of said defibrillation capacitor.

6. An apparatus for delivering an adaptive n-phasic defibrillation waveform to the heart comprising:

monitoring means for monitoring the electrical activity of the heart;

defibrillation electrode means adapted to be mounted on or about the heart;

defibrillation capacitor means connected to said defibrillation electrode means;

charging means connected to said defibrillation capacitor means for charging said defibrillation capacitor means to an initial voltage level;

n-phasic output means connected to said defibrillation capacitor means for delivering the voltage charged on said defibrillation capacitor means to said defibrillation electrode means in a sequence of consecutive phases of controlled durations and amplitudes to form an n-phasic defibrillation waveform;

control means connected to said n-phasic output means, said monitoring means, and said charging means, said control means being operable for monitoring and controlling the duration and polarity of each of said phases of said n-phasic defibrillation waveform and triggering said charging means to charge said defibrillation capacitor means upon said monitoring means detecting an arrhythmia of the heart, said control means further controlling said n-phasic output means to deliver said n-phasic defibrillation waveform in either a fixed-tilt mode or a fixed-duration mode;

programming means for setting a predetermined maximum amount of time for which a first phase of said n-phasic defibrillation waveform may last;

said control means being further operable for controlling said n-phasic output means to deliver said first phase of said n-phasic defibrillation waveform in a fixed-tilt delivery mode to the heart upon said monitoring means detecting an arrhythmia of the heart so that said first phase terminates upon the amplitude of said first phase decreasing to a preset level, triggering said n-phasic output means to terminate said first phase and switching to a fixed-duration delivery mode if the time duration of said first phase meets or exceeds said predetermined maximum amount of time, controlling said n-phasic output means to deliver phases of said n-phasic defibrillation waveform, subsequent said first phase, to the heart and in alternating polarities in a fixed-duration delivery mode if the time duration of said first phase is at least equal to said predetermined maximum amount of time whereby each of said subsequent phases terminates upon the duration of the phase meeting a preset value, and triggering said n-phasic output means to deliver phases of said n-phasic defibrillation waveform, subsequent said first phase, to the heart and in alternating polarities in a fixed-tilt mode if the time duration of said first phase is at least equal to said predetermined maximum amount of time whereby each of said subsequent phases terminates upon the level of the phase decreasing to a preset value.

7. The apparatus of claim 6, wherein said programming means is operable for presetting the total duration of said n-phasic defibrillation waveform, and presetting the waveshape of each of said phases of said n-phasic defibrillation waveform by setting the duration of each of said phases as a percentage of the total duration of said n-phasic defibrillation waveform.

8. The apparatus of claim 6, wherein said programming means is operable for presetting the waveshape of each phase subsequent said first phase by setting the duration of said each phase as a percentage of the duration of the first phase.

9. The apparatus of claim 8, wherein said programming means is operable for presetting the waveshape of each phase subsequent said first phase by determining said percentage by dividing the preset value for said each phase by the predetermined maximum amount of time of the first phase.

10. The apparatus of claim 6, wherein said programming means is operable for presetting the initial voltage level of said defibrillation capacitor means, said initial voltage level being an initial voltage level of said first phase of said n-phasic defibrillation waveform, and for presetting the waveshape of each of said phases of said n-phasic defibrillation waveform by setting a maximum voltage of each of said phases as a percentage of the initial voltage level of said defibrillation capacitor.

11. A method for delivering an adaptive n-phasic defibrillation waveform to the heart in either a fixed-tilt mode or a fixed-duration mode, the method comprising the steps of:
   monitoring the electrical activity of the heart;
   setting a predetermined maximum amount of time for which a first phase of said n-phasic defibrillation waveform may last;
   charging a defibrillation capacitor to an initial voltage level upon detecting an arrhythmia of the heart;
   discharging said defibrillation capacitor for delivering said first phase of said n-phasic defibrillation waveform to the heart upon detecting an arrhythmia of the heart in a fixed-tilt delivery mode so that said first phase terminates upon the voltage level of said first phase decreasing to a preset level;
   monitoring the time duration and voltage level of said first phase;
   terminating said first phase and switching to a fixed-duration delivery mode if the time duration of said first phase is greater than or equal to said predetermined maximum amount of time before said voltage level of said first phase decreases to said preset level;
   delivering phases of said n-phasic defibrillation waveform, subsequent said first phase, to the heart in a fixed-duration delivery mode if the time duration of said first phase is greater than or equal to said predetermined maximum amount of time; and
   delivering phases of said n-phasic defibrillation waveform, subsequent said first phase, to the heart in a fixed-tilt mode if the time duration of said first phase does not meet or exceed said predetermined maximum amount of time before the voltage level of said first phase decreases to said preset level.

12. The method of claim 11, and further comprising the step of alternating the polarity of the voltage of consecutive phases of said n-phasic defibrillation waveform.

13. A method for delivering an adaptive n-phasic defibrillation waveform to the heart comprising the steps of:
   monitoring the electrical activity of the heart;
   setting a predetermined maximum amount of time for which a first phase of said n-phasic defibrillation waveform may last;
   charging a defibrillation capacitor to an initial voltage level upon detecting an arrhythmia of the heart;
   discharging said defibrillation capacitor for delivering said first phase in a first polarity to the heart in a fixed-tilt delivery mode upon detecting an arrhythmia of the heart so that said first phase terminates upon the voltage level of said first phase decreasing to a preset level;
   monitoring the time duration and voltage level of said first phase;
   terminating said first phase and switching to a fixed-duration delivery mode if the time duration of said first phase is greater than or equal to said predetermined maximum amount of time before said voltage level of said first phase decreases to said preset level;
   delivering a second phase in a second polarity opposite to said first polarity if the time duration of said first phase is greater than or equal to said predetermined maximum amount of time before said voltage level of said first phase decreases to said preset level;
   delivering phases of said n-phasic defibrillation waveform, subsequent said first phase, to the heart and in alternating polarities in a fixed-duration delivery mode if the time duration of said first phase is greater than or equal to said predetermined maximum amount of time; and
   delivering phases of said n-phasic defibrillation waveform, subsequent said first phase, to the heart and in alternating polarities in a fixed-tilt mode if the time duration of said first phase does not meet or exceed said predetermined maximum amount of time before the voltage level of said first phase decreases to said preset level.

14. The method of claim 13, and further comprising the steps of:
   presetting the number of phases of said n-phasic defibrillation waveform;
   counting the number of phases before they are delivered to the heart; and
   terminating shock delivery if said counted number of phases exceeds said preset number of phases.

15. A method for delivering an adaptive n-phasic defibrillation waveform to the heart comprising the steps of:
   delivering a first phase to the heart in a first polarity;
   monitoring the level and duration of said first phase;
   declaring that the patient has a relatively low system impedance or capacitance if said first phase decays to a preset value within a maximum period of time and delivering phases subsequent to said first phase in alternating polarities and in a fixed-tilt delivery mode whereby each of said subsequent phases terminates upon the level of the phase decaying to a preset value; and
   declaring that the patient has a relatively high system impedance or capacitance if said first phase does not decay to said preset value within said maximum period of time and delivering phases subsequent to said first phase in alternating polarities in a fixed-duration delivery mode whereby each of said subsequent phases terminates upon the duration of the phase meeting a preset value.

* * * * *